United States Patent
Jadhav et al.

(10) Patent No.: US 7,229,949 B2
(45) Date of Patent: Jun. 12, 2007

(54) SAFE DELIVERY SYSTEM FOR AGRICULTURALLY ACTIVE MATERIAL

(75) Inventors: Prakash Mahadev Jadhav, Mumbai (IN); Jaidev Rajnikant Shroff, Mumbai (IN)

(73) Assignee: United Phosphorus, Ltd., Mumbai (IN)

( * ) Notice: Subject to any disclaimer, the term of this patent is extended or adjusted under 35 U.S.C. 154(b) by 0 days.

(21) Appl. No.: 11/168,994

(22) Filed: Jun. 29, 2005

(65) Prior Publication Data

US 2006/0003014 A1 Jan. 5, 2006

Related U.S. Application Data

(60) Provisional application No. 60/583,616, filed on Jun. 30, 2004.

(51) Int. Cl.
 *A01N 25/28* (2006.01)
 *A01N 37/10* (2006.01)
 *A01N 47/40* (2006.01)
 *A01N 53/08* (2006.01)
 *A01P 7/04* (2006.01)

(52) U.S. Cl. ............... 504/359; 424/408; 424/493; 514/65; 514/521; 514/544; 514/778; 514/963

(58) Field of Classification Search ............ 504/359; 424/408, 493; 514/65, 521, 544, 778, 963
See application file for complete search history.

(56) References Cited

U.S. PATENT DOCUMENTS

| 4,285,720 A | 8/1981 | Scher |
| 5,741,521 A * | 4/1998 | Knight et al. ............ 424/488 |
| 6,133,197 A | 10/2000 | Chen |
| 2002/0044968 A1 * | 4/2002 | van Lengerich ........... 424/469 |

* cited by examiner

*Primary Examiner*—S. Mark Clardy
(74) *Attorney, Agent, or Firm*—Jones, Tullar & Cooper, P.C.

(57) ABSTRACT

A safe delivery system of agriculturally active material is formed using an encapsulation process. A microencapsulated suspension of agriculturally active material includes an encapsulating agent formed from a graft copolymer of starch and at least one vinyl monomer.

30 Claims, No Drawings

SAFE DELIVERY SYSTEM FOR AGRICULTURALLY ACTIVE MATERIAL

CROSS-REFERENCE TO RELATED APPLICATION

This application claims the benefit, under 35 U.S.C. 119(e), of U.S. Provisional Application No. 60/583,616 filed Jun. 30, 2004, the contents of which are incorporated herein by reference.

BACKGROUND OF THE INVENTION

1. Field of Invention

The present invention relates to a safe delivery system of agriculturally active material and a process for preparing microencapsulated suspension of agriculturally active material, preferably including pyrethroids wherein the encapsulating agent is a graft copolymer of a starch and at least one vinyl monomer.

2. Description of Related Art

In the agrochemical industry, insecticides are formulated as dust, emulsifiable concentrates, suspension concentrates, wettable powders or wettable granules, and water dispersible granules depending on the properties of the active ingredient and the target pest species and market. Insecticides such as lambda cyhalothrin, cypermethrin, fenvalerate, permethrin, alpha-cypermethrin, and similar compounds, which are moderately toxic in the technical form, have a high skin irritant property and in some cases may provoke an adverse skin reaction such as burning, tingling, numbness or prickling sensation., also generally known as paraesthesia. These skin irritant properties are most pronounced in the areas of an operator's face, hand, and neck during application of these insecticides. For delivering such agriculturally active materials to a target, encapsulation or microencapsulation is one of the safest modes. Encapsulation, or more specifically microencapsulation, is increasingly being used to target specific insects, as it also provides a safer handling of toxic fungicides and insecticides. A microcapsule is a $10^{-3}$ m to $10^{-9}$ m diameter particle, composed of an inner core material and an outer shell. Microencapsulation of these kinds of agrochemicals can also be advantageous in providing the active material in relatively more concentrated form than the emulsifiable concentrate, wettable powder etc., at the same time reducing the amount of other ingredients such as surfactants, solvents, dye(s) etc.

Microencapsulation of a number of different agriculturally active materials and pesticides has been known for many years by using various processes or techniques for microencapsulation. The general technology for forming microcapsules is divided into two classifications known as physical methods and chemical methods. The physical methods are spray coating, spray drying, pan coating, rotary disk atomization etc. The chemical microencapsulation methods are phase separation, interfacial polymerization, simple and complex coacervation method etc.

The total process of microencapsulation covers three separate steps on a time scale. The first step consists of forming a shell around a core material. The second step involves keeping the core inside the shell material so that it does not release. Also, the shell material must prevent the entrance of undesirable materials that may harm the core. And finally, it is necessary to release the core material beginning at the right time, stage and at the right rate.

Prior encapsulation methods include a process for the preparation of microencapsulated water-immiscible material, including pesticides and other agrochemicals, by interfacial polymerization techniques using one or more polyisocyanates and producing microcapsules having a droplet size of from 0.5 to about 4000 microns, which provides a controlled or sustained release (over weeks) of the active ingredients. This type of controlled released encapsulation is useful in the case of soil application. Whereas, fast release is required in the case of foliar applications.

Another encapsulation method includes a process of encapsulation of a water-immiscible material. i.e. pyrethroid insecticide, within discreet capsules of polyurea prepared from an aromatic diisocyanate. However, the untreated isocyanate, if any, of said isocyanates may cause skin/eye irritation due to its high toxicity Release rates are governed by the capsule particle size, the thickness of the wall and the permeability of the wall. Small particles with thin walls and low cross-linking density allow the fastest possible release.

Starch is a cheap and natural polymer and is a renewable degradable carbohydrate biopolymer that can be taken from various sources by environmentally sound processes. Starch is hydrophilic and a partially water soluble polymer. Starch-based biodegradable low-density polyethylene (LDPE) films have been used for graft copolymerization of vinyl acetate with ceric ammonium nitrate. Additionally, it is known to graft vinyl acetate and starch acetate with a high degrees of substitution copolymerized to prepare a kind of biodegradable material.

BRIEF SUMMARY OF THE INVENTION

The present invention provides an encapsulation process for an agriculturally active material, preferably a pyrethroid, with a graft copolymer of a starch and at least one vinyl monomer. The polymers used in the present encapsulation process are biodegradable polymer. Starch is hydrophilic and a partially water soluble polymer. In the present encapsulation process, the starch provides a polymeric outer shell to an inner core material after grafting with the vinyl monomer. The present invention provides an encapsulation process for agriculturally active material without using any diisocyanate/isocyanate, The present encapsulation process has several advantages over the prior methods for encapsulating material. The present encapsulation process provides a safe delivery system of agriculturally active material by means of microencapsulation. The present encapsulation process uses graft polymerization. Preferably, the present encapsulation process provides a process of microencapsulation of agriculturally active material by starch graft polymerization so as to provide microcapsules of lambda cyhalothrin. Most preferably, microcapsules of lambda cyhalothrin are formed by producing an encapsulating film formed from a graft copolymer including a starch and at least one vinyl monomer. In a preferred process the vinyl monomer is a vinyl acetate monomer present as a free radical initiator. The present encapsulation process preferably provides for the microencapsulation of a pyrethroid, such as lambda cyhalothrin.

DETAILED DESCRIPTION OF THE INVENTION

The present encapsulation process provides a safe delivery system for an agriculturally active material, preferably by microencapsulation, for preparing microcapsules of an agriculturally active water immiscible material, where an outer shell of a capsulated inner core material is a natural modified polymer. The agriculturally active material is preferably a pyrethroid, most preferably lambda cyhalothrin. However, the encapsulated material may be a combination of two or more such agriculturally active material.

The encapsulation process for preparing microencapsules of an agriculturally active water immiscible material comprises the following steps: a) preparing an organic phase including an agriculturally active water immiscible material and a solvent, in the presence of at least one surfactant; b) preparing an aqueous phase including water, a starch, and a protective colloid; c) heating the aqueous phase to obtain a gelatinized aqueous phase followed by cooling; d) adding the organic phase of step (a) into the gelatinized aqueous phase of step (c) to form an oil-in-water emulsion; e) adding an initiator to the oil-in-water emulsion of step (d) in an inert atmosphere; f) adding a vinyl monomer for graft reaction to occur and resulting in obtaining a microencapsulated suspension; g) neutralizing the microencapsulated suspension of step (f) followed by adding a structuring agent. In a preferred embodiment, the following encapsulation process is used to prepare the microencapsulated suspension:

a) preparing an organic phase comprising an agriculturally active water immiscible material to be encapsulated and a solvent, in the presence of at least one surfactant by continuously stirring to get a clear solution;

b) preparing an aqueous phase comprising water, a starch, a protective colloid, a biocide, an optional anti freezing agent and a surfactant, c) heating the aqueous phase at a temperature of 65–85° C. for 15–45 minutes to obtain a gelatinized aqueous phase and cooling the gelatinized aqueous phase to room temperature;

d) adding the organic phase of step (a) into the gelatinized aqueous phase of step (c) slowly with high shear to form an oil-in-water emulsion, wherein said oil-in-water emulsion includes oil droplets having a size less than 5 microns;

e) adding an initiator to generate free radicals to maintain the oil-in-water emulsion at a pH between 2–5, and simultaneously purging an inert gas to keep the process oxygen-free, at a temperature range between 15–30° C.;

f) adding a vinyl monomer slowly at a constant rate such that a grafting reaction occurs at the interface of the organic phase and gelatinized aqueous phase, while maintaining the process at a temperature range of 15–30° C. and forming a microencapsulated suspension;

g) neutralizing the microencapsulated suspension with an organic aliphatic amine and stirring the same for 30–60 minutes after adding a structuring agent to obtain a desired microencapsulated suspension of agriculturally active material.

The material used for the microcapsule outer shell is a starch grafted with at least one vinyl monomer, which provides a biodegradable microcapsule shell material. A vinyl monomer is defined herein to include a monomer with at least one vinyl group. The ratio between the starch and the vinyl monomer is 1:1 to 1:5 and preferably the ratio is 1:1 to 1:3 and more preferably is 1:1 to 1:2.

The preferred starch is a hydrophilic and partially water soluble polymer, which is used as a polymer outer shell to an inner core material after grafting with the vinyl monomer. The starch used is preferably starch from corn, wheat, potatoes, rice, sago and sorghum. Additionally, the starch may include suitable starch derivatives, preferably starch ethers, starch esters, cross-link starch and oxidized starch.

The vinyl monomer used to produce a starch graft polymer is any monomer polymerizable on the thinned gelatinized starch through a free radical initiator. The vinyl monomer or combination of vinyl monomers can be chosen such that starch graft co-polymers particles are dispersed in an aqueous continuous phase. The preferred vinyl monomers include, but are not limited to, vinyl halide, vinyl ethers, alkyl vinyl ketones, N-Vinyl carbzole, N-Vinyl pyrolidone, Vinyl pyrridine, styrene, alkyl styrene, acrylic acid, alkyl methylacrylates, acrylamides, substituted acrylamides, vinyledenehalides, itaconic acid, 1, 3-butadine and the like. When single vinyl monomers are used to form the graft polymer, the preferred vinyl monomer preferably includes, but is not limited to acrylonitrile, methyl methacrylate, vinyl acetate, 2-ethyl hexyl acrylate and the lower alkyl acrylates such as methyl acrylates, ethyl acrylate, and n-butyl acrylates.

The surfactant is preferably an anionic or non-ionic surfactant with HLB range about 12–16 that is high enough to form stable oil/water emulsion. Suitable surfactants include, but are not limited to, polyethylene glycol ethers of linear alcohol, ethoxylated nonyl-phenol, naphthalene sulphonates, salts of long chain alkyl benzene sulphonate, block-co-polymers of propylene oxide and ethylene oxide, and anionic/nonionic blends.

Suitable solvents include, but are not limited to, alkyl benzene, methylnapthalene, alkyl esters of pthalic acid, trimellitic acid, aromatic hydrocarban such as xylene, naphthalene mix of aromatics aliphatic or cycloaliphatic hydrocarbon such as hexane, heptane, phthalates, ketones such as cyclohexanone or acetophenone or chlorinated hydrocarbons, vegetable oils or mix of such two or more solvents.

The free radical initiator is any polymerization initiator which acts to initiate free radical polymerization on gelatinized thinned starch to the substantial exclusion of initiation of homo or co-polymerization of the monomer or mixture of monomer utilized to form starch graft co-polymer is suitable initiator. Ceric ammonium nitrate is an example of such initiator. Another preferred initiation is the combination of hydrogen peroxide and acetate ion.

The protective colloid can be selected from a wide range of materials which must have the property of absorbing on the surface of oil droplets. The suitable colloid includes, but is not limited to, one or more methyl cellulose, polyvinyl alcohol, poly-acrylamide, poly (methyl vinyl ether/maliec anhydride), graft co-polymers, alkali metals and alkaline earth metals of alkyl naphthalene sulphonate. Preferably, however, the protective colloid is selected from alkali metals and alkaline earth metals of alkyl naphthalene sulphonate.

Antifreezing agent is being used to make the formulation workable in any atmosphere. Antifreezing agent may include, but are not limited to, ethylene glycol, diethylene glycol, propylene glycol, glycerol etc.

The biocide is preferably methyl paraben, ethyl paraben, formaldehyde, glutaraldehyde, 2-bromo-2-nitropropane-1, 3 diol, 4, 4 dimethyloxazolide, 7-ethybicyclo oxazolide and others.

The neutralizing agent is preferably an organic aliphatic amine such as tri-ethanol amine.

The structuring agent is preferably selected from xanthan gum, guar gum, arabic gum, HPMC, CMC and others.

EXAMPLES:

The following are non-limiting examples illustrating the present encapsulation process and safe delivery system.

Examples: 1

| 1) Organic phase: | |
|---|---|
| a) Active content - Lambda Cyhalothrin (Purity 95%) | 52.63 g |
| b) Solvent - Solvesso-200 | 52.00 g |
| c) Anionic surfactant - Calcium salt of alkyl benzene sulfonic acid | 10.00 g |
| d) Nonionice Surfactant - Polyoxyethylene Nonyl phenol-9 moles | 10.00 g |
| 2) Aqueous Phase: | |
| a) Natural Polymer - Starch | 05.00 g |
| b) Antifreezing agent - PEG | 25.00 g |
| c) Anionic Surfactant - Geropon TA 72 | 10.00 g |
| d) Dispersant - Emulsol 101 | 50.00 g |
| e) Biocide - Methyl paraben | 05.00 g |
| f) Structuring agent - Xanthan gum (2% gel) | 20.00 g |
| g) Vinyl Monomer - Vinyl acetate | 10.00 g |
| h) Initiator - Ceric ammonium nitrate (10% in 1 Normal HNO3) | 20.00 g |
| i) pH modifier - Triethanol amine | 2.500 g |
| j) Diluent - Water | QS |
| | 500.00 g |

The above composition can be prepared by following the present encapsulation process as follows:

The organic phase was prepared by mixing 52.63 g of lambda cyhalothrin technical in 52.00 g Solvesso-200 along with 10.00 g of the calcium salt of alkyl benzene sulfonic acid (anionic surfactant) and 10.00 g of Polyoxyethylene Nonyl phenol-9 moles (nonionic surfactant) by continuously stirring to get a clear solution;

The aqueous phase was prepared by dissolving 10.00 g of Geropon TA-72 and 25.00 g of PEG along with 50.00 g Emulsol-101 and 5.00 g Starch in water and this was heated to 70–90° C. to form a gelatinized aqueous phase, which was cooled to 15–30° C.;

The organic phase was added into the gelatinized aqueous phase slowly with high shear to form an oil-in-water emulsion having oil droplet with a size less than 5 microns and 20.00 g free radical initiator was added into this oil-in-water emulsion and stirred while an inert gas (N$_2$) was purged to keep the process oxygen-free.

The process was maintained at a temperature range of 22–25° C. and at a pH maintained at 2.9–3.0 with the help of concentrated HNO$_3$.

Thereafter 10 g of vinyl acetate monomer was added at a constant rate such that a grafting reaction occurs at the interface of the organic phase and gelatinized aqueous phase, while maintaining the process at a temperature range of 15–30° C. and a microencapsulated suspension is formed.

After the grafting reaction was completed, the microencapsulated suspension was neutralized with 2.50 g of triethanaolamine.

Thereafter, 20.00 g of Xanthan gum (2% gel) was added to the microencapsulated suspension.

The microencapsulated suspension was stirred for an additional 30–60 minutes to get produce microcapsules of lambda cyhalothrin having an oil droplet size less than 5 microns.

Examples: 2

| 1) Organic phase: | |
|---|---|
| a) Active Content - Lambda Cyhalothrin (Purity 95%) | 105.00 g |
| b) Solvent - Solvesso-200 | 100.00 g |
| c) Anionic Surfactant - Calcium salt of alkyl benzene sulfonic acid | 12.00 g |
| d) Nonionic Surfactant - Polyoxyethylene Nonyl phenol-9 moles | 12.00 g |
| 2) Aqueous Phase: | |
| a) Natural Polymer - Starch | 08.00 g |
| b) Antifreezing Agent - PEG | 25.00 g |
| c) Anionic surfactant - Geropon TA 72 | 10.00 g |
| d) Dispersent - Emulsol 101 | 50.00 g |
| e) Biocide - Methyl paraben | 05.00 g |
| f) Structuring agent - Xanthan gum | 20.00 g |
| g) Vinyl monomer - Vinyl acetate | 16.00 g |
| h) Initiator - Ceric ammonium nitrate (10% in 1 Normal HNO3) | 20.00 g |
| i) pH modifier - Triethanol amine | 2.500 g |
| j) Diluent - Water | QS |
| | 500.00 g |

The above composition can be prepared by following the process as described in Example-1 except keeping the system at 25° C. and pH 3.2 (adjusted by using concentrated HNO$_3$) after initiator was added.

Examples: 3

| 1) Organic phase: | |
|---|---|
| a) Active Content - Lambda Cyhalothrin (Purity 95%) | 158.00 g |
| b) Solvent - Solvesso-200 | 150.00 g |
| c) Anionic Surfactant - Calcium salt of alkyl benzene sulfonic acid | 15.00 g |
| d) Nonionic Surfactant - Polyoxyethylene Nonyl phenol-9 moles | 15.00 g |
| 2) Aqueous Phase: | |
| a) Natural Polymer - Starch | 12.00 g |
| b) Antifreezing agent - PEG | 25.00 g |
| c) Anionic Surfactant - Geropon TA 72 | 10.00 g |
| d) Dispersant - Emulsol 101 | 50.00 g |
| e) Biocide - Methyl paraben | 05.00 g |
| f) Structuring agent - Xanthan gum | 20.00 g |
| g) Vinyl Monomer - Vinyl acetate | 24.00 g |
| h) Initiator - Ceric ammonium nitrate (10% in 1 Normal HNO3) | 20.00 g |
| i) pH modifier - Triethanol amine | 2.500 g |
| j) Diluent - Water | QS |

The above composition can be prepared by following the process as described in Example-1 except keeping the system at 25° C. and pH 3.8 (adjusted by using concentrated HNO$_3$) after initiator was added.

Examples: 4

| 1) Organic phase: | |
|---|---|
| a) Active content - Lambda Cyhalothrin (purity 95%) | 52.63 g |
| b) Solvent - Solvesso-200 | 52.00 g |

-continued

| | |
|---|---|
| c) Anionic surfactant - Calcium salt of alkyl benzene sulfonic acid | 10.00 g |
| d) Nonionic Surfactant - Polyoxyethylene Nonyl phenol-9 moles | 10.00 g |
| 2) Aqueous Phase: | |
| a) Natural Polymer - Starch | 05.00 g |
| b) Antifreezing agent - PEG | 25.00 g |
| c) Anionic surfactant - Geropon TA 72 | 10.00 g |
| d) Dispersent - Emulsol 101 | 50.00 g |
| e) Biocide - Methyl paraben | 05.00 g |
| f) Structuring agent - Xanthan gum | 20.00 g |
| g) Vinyl Monomer - Vinyl acetate | 10.00 g |
| h) Initiator - Ceric ammonium nitrate (10% in 1 Normal HNO3) | 02.00 g |
| i) pH modifier - Triethanol amine | 2.500 g |
| j) Diluent - Water | QS |
| | 500.00 g |

The above composition can be prepared by following the process as described in Example -1 except keeping the system at 25° C. and pH 4.0 (adjusted by using concentrated $HNO_3$) after initiator was added.

Examples 5

| | |
|---|---|
| 1) Organic phase: | |
| a) Active content - Lambda Cyhalothrin (purity 95%) | 52.63 g |
| b) Solvent - Solvesso-200 | 52.00 g |
| c) Anionic surfactant - Calcium salt of alkyl benzene sulfonic acid | 10.00 g |
| d) Nonionic Surfactant - Polyoxyethylene Nonyl phenol-9 moles | 10.00 g |
| 2) Aqueous Phase: | |
| a) Natural Polymer - Starch | 05.00 g |
| b) Antifreezing agent - PEG | 25.00 g |
| c) Anionic surfactant - Geropon TA 72 | 10.00 g |
| d) Dispersent - Emulsol 101 | 50.00 g |
| e) Biocide - Methyl paraben | 05.00 g |
| f) Structuring agent - Xanthan gum | 20.00 g |
| g) Vinyl Monomer - Vinyl acetate | 10.00 g |
| h) Initiator - Ceric ammonium nitrate (10% in 1 Normal HNO3) | 10.00 g |
| i) pH modifier - Triethanol amine | 2.500 g |
| j) Diluent - Water | QS |
| | 500.00 g |

The above composition can be prepared by following the process as described in Example-1 except keeping the system at 25° C. and pH 3.0 (adjusted by using concentrated $HNO_3$) after initiator was added.

Although the present invention has been disclosed in terms of a preferred embodiment, it will be understood that numerous additional modifications and variations could be made thereto without departing from the scope of the invention as defined by the following claims:

We claim:

1. An encapsulation process for preparing a microencapsulated suspension for a safe delivery system of an agriculturally active material, comprising the steps of:
   a) preparing an organic phase comprising an agriculturally active water immiscible material and a solvent, in the presence of at least one surfactant;
   b) preparing an aqueous phase comprising water, a starch, and a protective colloid;
   c) heating the aqueous phase to obtain a gelatinized aqueous phase followed by cooling;
   d) adding the organic phase of step (a) into the gelatinized aqueous phase of step (c) to form an oil-in-water emulsion;
   e) adding an initiator to the oil-in-water emulsion of step (d) in an inert atmosphere;
   f) adding a vinyl monomer for graft reaction to occur and resulting in obtaining a microencapsulated suspension;
   g) neutralizing the microencapsulated suspension of step (f) followed by adding a structuring agent.

2. The encapsulation process of claim 1, wherein the vinyl monomer is vinyl acetate.

3. The encapsulation process of claim 1, wherein the starch and the vinyl monomer are present in a ratio of 1:1 to 1:5.

4. The encapsulation process of claim 3, wherein the starch and the vinyl monomer are present in a ratio is 1:1 to 1:2.

5. The encapsulation process of claim 1, wherein said initiator is a free radical initiator.

6. The encapsulation process of claim 1, wherein said initiator is ceric ammonium nitrate.

7. The encapsulation process of claim 1, wherein said surfactant is an anionic surfactant or non-ionic surfactant or a combination thereof.

8. The encapsulation process of claim 1, wherein said step of preparing an aqueous phase further comprises a biocide.

9. The encapsulation process of claim 8, wherein said biocide is selected from the group consisting of methyl paraben, ethyl paraben and butyl paraben.

10. The encapsulation process of claim 1, wherein said protective colloid is an alkyl metal or an alkaline earth metals of alkyl naphthalene sulphonate.

11. The encapsulation process of claim 1, wherein said agriculturally active water immiscible material is a pyrethroid.

12. The encapsulation process of claim 11, wherein said agriculturally active water immiscible material is Lambda Cyhalothrin.

13. The encapsulation process of claim 1, wherein said step of preparing an aqueous phase further comprises a second surfactant.

14. The encapsulation process of claim 1, wherein said step of preparing an aqueous phase further comprises an anti-freezing agent.

15. The encapsulation process of claim 1, wherein said step of heating said aqueous phase includes heating at a temperature of 65–85° C.

16. The encapsulation process of claim 1, wherein said oil-in-water emulsion includes oil droplets having an oil droplet size of less than 5 microns.

17. The encapsulation process of claim 1, wherein said step of adding an initiator to the oil-in-water emulsion includes maintaining a pH between 2–5.

18. The encapsulation process of claim 1, wherein said step of adding an initiator to the oil-in-water emulsion includes maintaining a temperature ranging between 15–30° C.

19. The encapsulation process of claim 1, wherein said step of adding vinyl monomer includes maintaining a temperature of 15–30° C.

20. The encapsulation process of claim 1, wherein said step of neutralizing the microencapsulated suspension includes neutralizing with an organic aliphatic amine.

21. The encapsulation process of claim 1, wherein said step of preparing an organic phase includes continuously stirring to get a clear solution.

22. The encapsulation process of claim 1, wherein said step of heating the aqueous phase is followed by cooling to a temperature of 20–45° C.

23. The encapsulation process of claim 1, wherein said step of adding the organic phase of step (a) into the gelatinized aqueous phase of step (c) includes adding slowly with a high shear.

24. The encapsulation process of claim 1, wherein said inert atmosphere is an oxygen-free inert atmosphere.

25. A microcapsule for the safe delivery of an agriculturally active material comprising,
  a) an inner core including an agriculturally active material;
  b) an outer shell including a graft copolymer comprising a starch and at least one vinyl monomer.

26. The microcapsule of claim 25, wherein said agriculturally active material is a pyrethroid.

27. The microcapsule of claim 26, wherein said agriculturally active material is Lambda Cyhalothrin.

28. The microcapsule of claim 27, wherein said vinyl monomer is vinyl acetate monomer.

29. The microcapsule of claim 25, wherein the starch and the vinyl monomer are present in a ration of 1:1 to 1:5.

30. The microcapsules of claim 25, wherein said microcapsules have a size of less than 5 microns.

* * * * *